(12) United States Patent
Clark et al.

(10) Patent No.: US 6,839,404 B2
(45) Date of Patent: Jan. 4, 2005

(54) SYSTEM AND METHOD FOR POSITIONING AN ELECTRIC PORTAL IMAGING DEVICE

(75) Inventors: Charles Clark, Pleasanton, CA (US); Loren Lentz, Pleasanton, CA (US); Debra Penny, Livermore, CA (US); William J. Gibb, San Anselmo, CA (US); Todd H. Steinberg, Antioch, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 6 days.

(21) Appl. No.: 10/053,283

(22) Filed: Nov. 2, 2001

(65) Prior Publication Data

US 2003/0086529 A1 May 8, 2003

(51) Int. Cl.⁷ ................................................ A61N 5/10
(52) U.S. Cl. .................................................... 378/65
(58) Field of Search ............................ 378/65, 68, 55, 378/64, 108, 117, 116, 110, 112, 209, 97, 207

(56) References Cited

U.S. PATENT DOCUMENTS

| | | | |
|---|---|---|---|
| 4,995,068 A | 2/1991 | Chou et al. | |
| 5,138,647 A | 8/1992 | Nguyen et al. | ............. 378/189 |
| 5,233,990 A | 8/1993 | Barnea | .................... 128/653.1 |
| 5,712,482 A | 1/1998 | Gaiser et al. | .......... 250/363.08 |
| 5,754,622 A * | 5/1998 | Hughes | ....................... 378/65 |
| 5,784,431 A | 7/1998 | Kalend et al. | |
| 6,282,264 B1 * | 8/2001 | Smith et al. | ................ 378/189 |
| 6,345,114 B1 | 2/2002 | Mackie et al. | |

OTHER PUBLICATIONS

Herman, et al. "Clinical Use of Electronic Portal Imaging: Report of AAPM Radiation Therapy Committee Task Group 58," Medical Physics, May 2001, vol. 28, No. 5, pp. 712–737.

* cited by examiner

Primary Examiner—Tarifur R. Chowdhury
Assistant Examiner—Richard H Kim

(57) ABSTRACT

A portal imaging device positioning apparatus includes a portal imaging device positioner (255) attachable to a support (256). The portal imaging device positioner (255) is adapted to vertically adjust an imaging panel (250) in a treatment or dosimetry mode to receive radiation through a body in the patient plane (8a), and adjust the panel in a physics mode to receive radiation at the patient plane (8a).

14 Claims, 7 Drawing Sheets

SYSTEM AND METHOD FOR POSITIONING AN ELECTRIC PORTAL IMAGING DEVICE

CROSS REFERENCE TO RELATED APPLICATIONS

The present invention is related to co-pending U.S. patent application Ser. No. 10/053/369, titled "SYSTEM AND METHOD FOR MEASURING BEAM QUALITY AND DOSIMETRY USING ELECTRONIC PORTAL IMAGING," filed concurrently, and which is hereby incorporated by reference in its entirety as if fully set forth herein.

BACKGROUND OF THE INVENTION

The present invention relates to a radiation emitting device, and more particularly, to a system and method for evaluating beam quality during therapy using electronic portal imaging.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

Prior to receiving therapeutic doses of radiation, the patient must be positioned accurately and precisely. Radiotherapists have historically used laser pointers and radiographic film to ensure that patients are properly positioned. This can be a complex and time-consuming process. Electronic portal imaging devices (EPIDs) can now accomplish this step much more rapidly by providing instantaneous radiographic imaging on a computer monitor. Emerging applications for EPIDs require (1) accurate and precise positioning of the EPID, (2) adequate clearance between the EPID and the patient or treatment table, and (3) maneuverability of the EPID across a sufficiently wide range of motion.

SUMMARY OF THE INVENTION

A radiation therapy apparatus according to an embodiment of the present invention includes a portal imaging device having a portal imaging device positioner for accurately positioning the EPID, providing sufficient clearance, and maneuverability across a wide range of motion.

A portal imaging device positioning apparatus according to an embodiment of the present invention includes a portal imaging device positioner attachable to a support such as a telescoping boom. The portal imaging device positioner is adapted to vertically adjust an imaging panel in either a treatment or dosimetry mode to receive radiation that has passed through a body in the patient plane, and adjust the panel in a physics mode to receive radiation at the patient plane.

The portal imaging device positioner includes an imaging panel vertically attachable to a mounting unit which in turn is vertically attachable to a main vertical drive unit. The main vertical drive unit attaches adjustably to a support such as a telescoping boom. The mounting unit includes one or more hinges for deploying the imaging panel to a horizontal position. The main vertical drive unit includes a mounting cavity on a side adjacent the support. The main vertical drive unit is adjustable relative to the support to at least first and second positions within the mounting cavity.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

Figure 1:
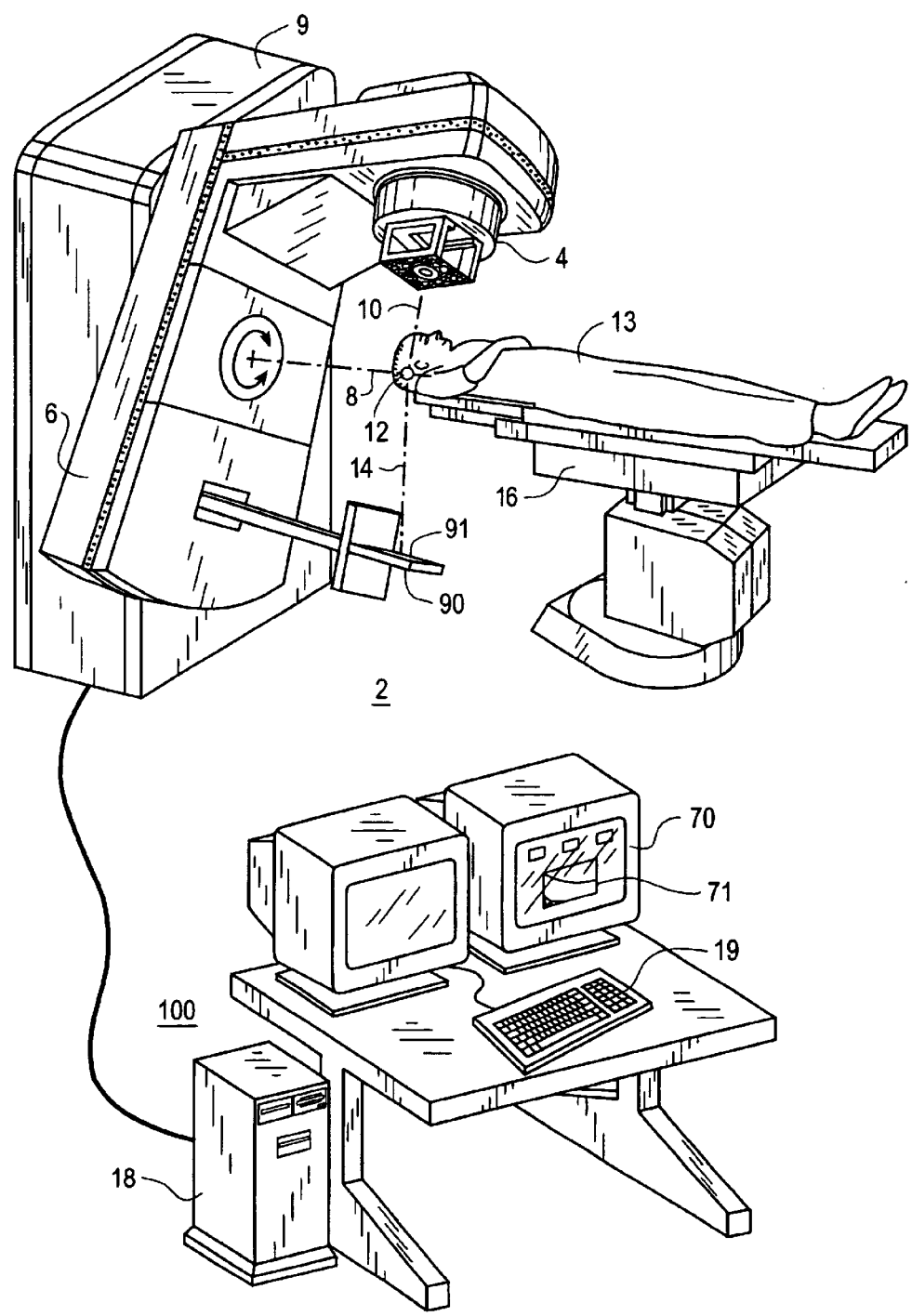
FIG. 1 is a diagram of a radiation treatment device according to an embodiment of the present invention.

Turning now to the drawings and, with particular attention to FIG. 1, a radiation treatment apparatus embodying the present invention is shown therein and generally identified by reference numeral 2. The radiation treatment apparatus 2 includes a beam shielding device (not shown) within a treatment head 4, a control unit in a housing 9 and a treatment unit 100. The radiation treatment device 2 includes a gantry 6 which can be swiveled around a horizontal axis of rotation 8 in the course of a therapeutic treatment. The treatment head 4 is fastened to projection of the gantry 6. A linear accelerator is located in the gantry 6 to generate the high powered radiation required for the therapy. The axis of the radiation beam emitted from the linear accelerator and the gantry 6 is designated by 10. Electron or photon radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter. Exemplary radiation treatment devices suitable for use with the teachings of the present invention are the Mevatron and Primus systems, available from Siemens Medical Systems, Inc.

A beam shielding device, such as a plurality of plates may be provided within the treatment head. Such plates are substantially impervious to the emitted radiation. The plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

It is noted that plates, although common, are not the only type of beam shielding devices available. For example, many radiation therapy devices include some form of beam collimator, wedge, compensator, jaw and/or other aperture device. An aperture device itself can act as the beam shielding device and the various beam shielding devices can be combined to limit the delivered radiation. The present invention can be used with any such arrangement and can also be used in dynamic conformal treatments in which the gantry, collimator, jaws and multileaf collimators could all be in motion during the radiation delivery.

The radiation treatment device 2 also includes a central treatment unit 100 which is typically located apart from the radiation treatment device 2. The radiation treatment device 2 is normally located in a different room to protect the therapist from radiation. The treatment unit 100 includes output devices such as at least one visual display unit or monitor 70 and an input device such as a keyboard 19. Data can be input also through data carriers such as data storage devices or a verification and recording or automatic setup system. Thus, display area 71 can cover a portion of the screen and can be designed as a window or as an icon. In addition to the measured delivered radiation, the prescribed radiation can also be shown on the screen. The display of the measured delivered radiation may be carried out in real time. Thus, at any time during treatment, the amount of delivered radiation can be verified. In addition, at the end of a treatment, the overall delivered radiation can be verified with the prescribed radiation. This can be initiated automatically with a software program capable of detecting the end of a treatment, or this can be initiated manually by, for example, a therapist. Instead of or in addition to monitor 70, other output devices, such as a printer, can be utilized.

The treatment processing unit 100 is typically operated by the therapist who administers actual delivery of radiation treatment as prescribed by an oncologist by using the keyboard 19 or other input device. The therapist enters into the control unit of the treatment unit 100 the data that defines the radiation dose to be delivered to the patient, for example, according to the prescription of the oncologist. The program can also be input via another input device, such as a data storage device. Various data can be displayed before and during the treatment on the screen of the monitor 70.

In addition, a portal imaging system 90 may be attached to the gantry 6. Because the portal imaging system 90 is mounted on the gantry 6, portal images can be obtained at any gantry angle and during rotation of the gantry 6. The portal imaging system may include a flat panel, amorphous silicon detector implemented as one or more arrays of photo-sensors.

The portal imaging system includes a detector unit 91 capable of measuring the radiation exiting the object 13. The amount of radiation exiting object 13 can be used to verify the radiation treatment in a treatment mode. Thus, the detector unit 91 is used to gather the patient's exit dose information. The radiation dose is then reverse calculated by the CPU 18. The delivered radiation dose is then compared to the planned delivery dose. If these dose amounts match, the prescription was executed as planned. If the amounts do not match, measures can be taken for correction.

In addition, the portal imaging system allows characterization of all beams produced by the linac in a characterization or physics mode. The beam data includes relative beam profiles and absolute dosimetric quantities with varying machine conditions (fields sizes, energies, beam modifiers, dose rates, setup conditions, etc.). Once the data has been collected, it is used to set up dosimetry tables and to commission the treatment planning computer used for dose calculations.

Figure 2:
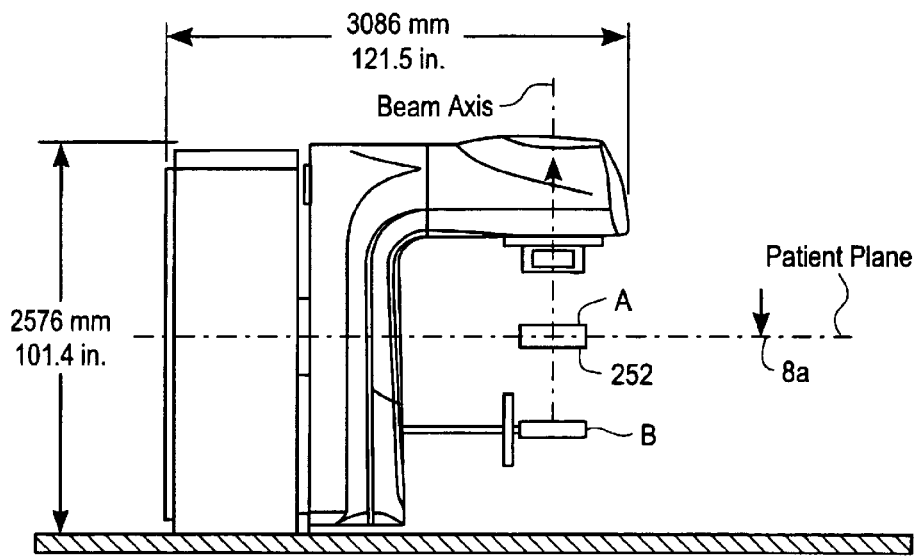
FIG. 2 is a diagram illustrating the adjustability of a portal imaging device positioner according to an embodiment of the present invention.

To properly commission the medical linac, data must be collected under normal clinical conditions of the machine. This data must be collected at various depths with respect to the isocentric plane. A portal imaging system according to embodiments of the present invention allows both commissioning the linac and measurement of patient exit dosimetry. More particularly, as will be explained in greater detail below, the portal imaging device platform 252 is adjustable in a vertical direction and, as such, is usable for both device commissioning and patient dosimetry. That is, as shown in FIG. 2, the portal imaging device platform 252 is adjustable in a position A in the patient plane 8a, for use in commissioning the machine, and in a position B for use in dosimetry. The treatment unit 100 may be used for controlling deployment of the portal imaging system from one mode to the other.

Figure 3A:
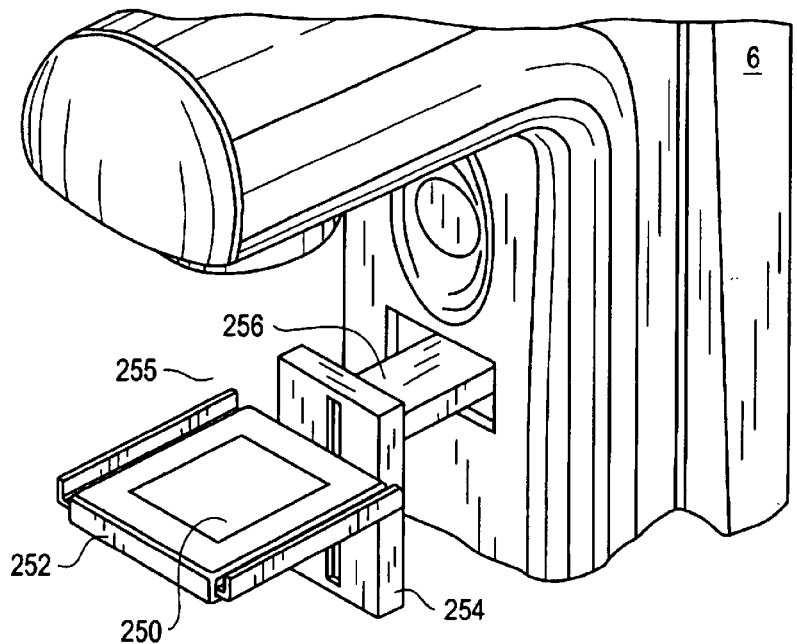
FIG. 3A and FIG. 3B illustrate a portal imaging device positioner according to an embodiment of the present invention.

Turning now to FIG. 3A, a diagram of a portal imaging device positioner according to an embodiment of the present invention is shown. The portal imaging device positioner 255 includes a platform 252 which may be embodied as a collision bumper to protect against injury or damage. Underneath the collision bumper 252 is the EPID panel 250. The collision bumper 252 and EPID panel 250 ride vertically on the vertical drive unit or backplane 254. The backplane 254 itself can be moved in and out from the gantry. These movements are all motorized and can be controlled manually or automatically by the treatment control system 100.

Figure 3B:
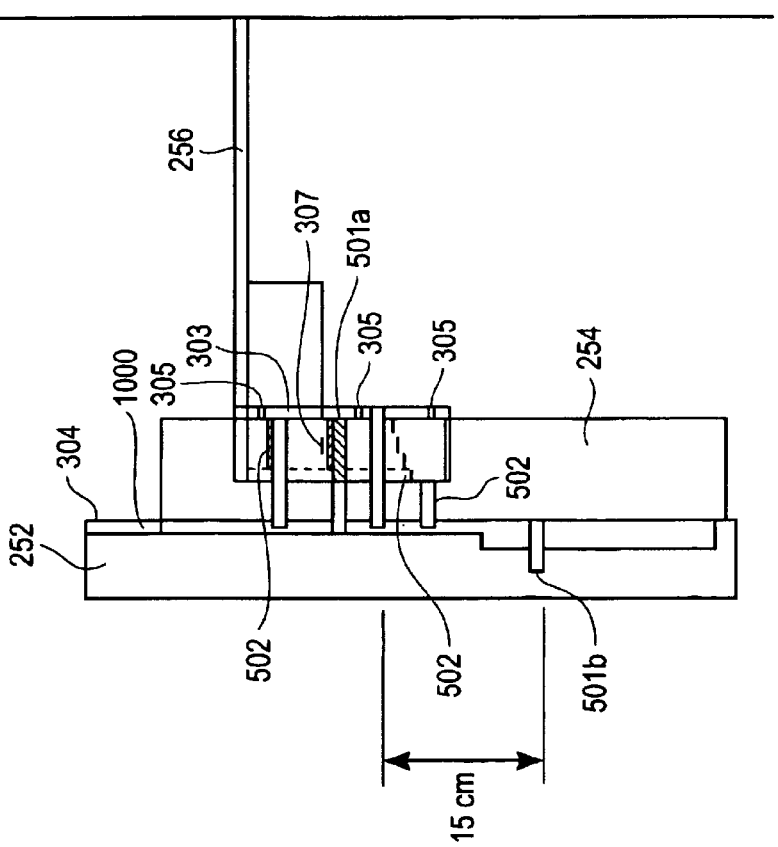

FIG. 3B illustrates various components of the portal imaging device positioner in a schematic view. As shown, the portal imaging device positioner attaches to the gantry 6 by a support such as a telescoping boom 256. A computer-controlled motor within the gantry 6 (not shown) may be used to extend and retract the portal imaging device positioner. The imaging platform 252 mounts to the vertical drive unit 254 via the mounting unit 1000. The platform 252 is extendable into a horizontal position using one or more hinges 304. The extension into horizontal position may be accomplished using a computer-controlled motor (not shown).

In the embodiment illustrated, the vertical drive assembly 254 includes a mounting cavity 307 to allow for vertical movement of the platform 252 with respect to the telescoping boom 256. In a treatment mode, the top of the telescoping boom 256 is generally aligned with the top of the mounting cavity 307. In a physics mode, the bottom of the telescoping boom 256 is generally aligned with the bottom of the mounting cavity 307. A plurality of bolt holes 502 may be provided in the vertical drive assembly 254 to allow bolts to affix the vertical drive assembly 254 to the telescoping boom 256. Holes 501a, 501b may also be provided, to allow insertion of a "physics pin" to secure the platform 252 to the telescoping boom 256, as will be explained in greater detail below. Finally, a protective panel 303 may cover the mounting cavity 307 and may include a plurality of screw holes 305 for securing it in place.

Initially, in operation, the portal imaging device positioner is configured in a treatment mode. In this mode, the positioner is in place below the patient plane and the platform 252 can be deployed to receive radiation that passes through the patient. The top of the telescoping boom 256 is positioned substantially adjacent the top of the mounting cavity 307.

To change to the physics mode, the platform 252 is raised with respect to the vertical drive assembly 254 and telescoping boom 256. In one embodiment, the platform 252 is raised about 15 centimeters, so that the physics pin hole portions 501a, 501b are aligned.

The protective cover 303 is then removed, to allow installation of a physics pin into the physics hole. Bolts are then removed from the bolt holes 502 to allow movement of the vertical drive assembly 254 with respect to the telescoping boom 256. The main vertical drive assembly 254 is then raised relative to the telescoping boom 256. In particular, in one embodiment, the main vertical drive assembly 254 is raised 15 centimeters, such that the bottom of the telescoping boom 256 is substantially adjacent the bottom of the mounting cavity 307. The bolts are then replaced, the physics pin is removed, and the panel can be deployed.

Adjustment of the portal imaging device positioner from treatment mode to physics mode is illustrated in greater detail with reference to FIGS. 4-9.

Figure 4:
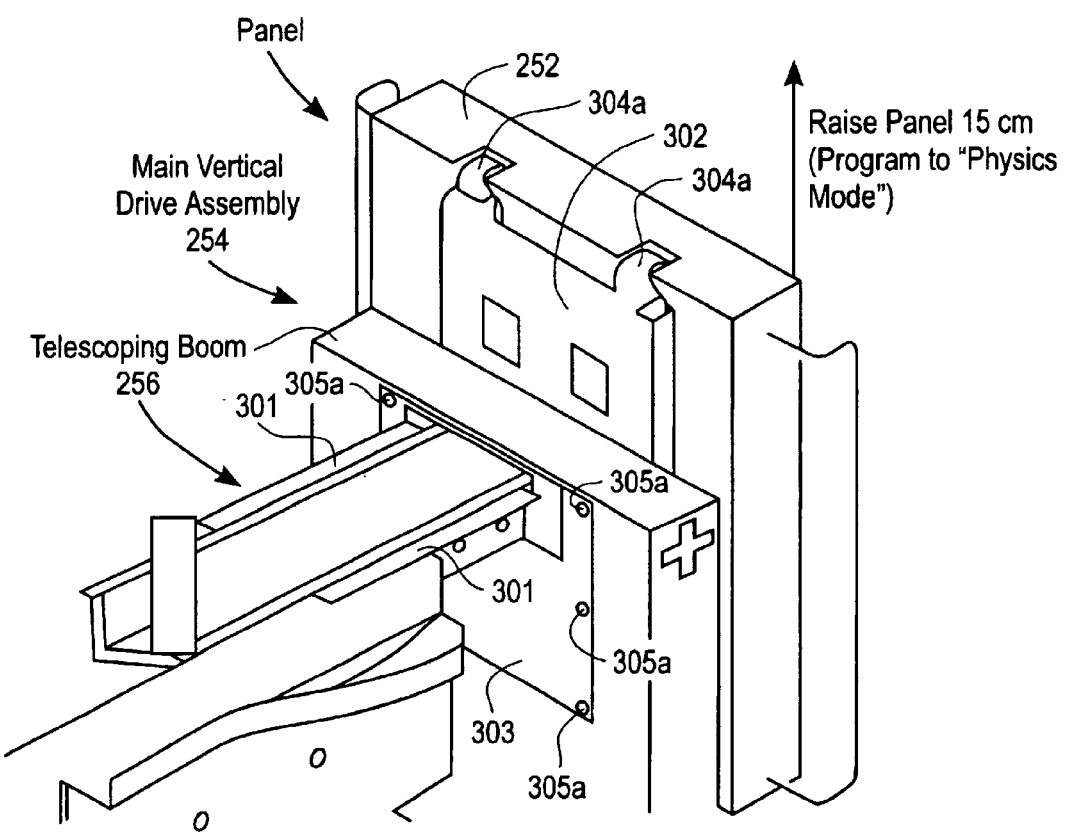
FIG. 4 is a diagram illustrating adjustment of a portal imaging device positioner according to an embodiment of the present invention.

As shown in FIG. 4, the main vertical drive assembly 254 is fixed to the telescoping boom 256 via one or more brackets 301 and a plate 303. The platform 252 attaches vertically to the main vertical drive assembly 254 via one or more hinges 304a, 304b. In operation, the platform 252 swings out horizontally on the hinges 304a, 304b, to receive radiation during both modes of operation. The platform 252 is typically stored vertically to save space. In addition, the plate 303 attaches to the main vertical drive assembly 254 via a plurality of fasteners, such as screws 305A, which fit into screw holes 305 (FIG. 3B). In on embodiment six (6) screws are provided (two of which are obscured in the figure by the telescoping boom 256).

To change the mode of operation from the treatment mode to the physics mode, the vertical drive assembly 254 is adjusted such that the platform 252 can be fixed in a higher position, i.e., in the patient plane. Initially, the platform 252 is raised from a default position to the physics position in the direction of the arrow 306. In one embodiment of the present invention, the platform 252 is raised about 15 centimeters.

Figure 5:
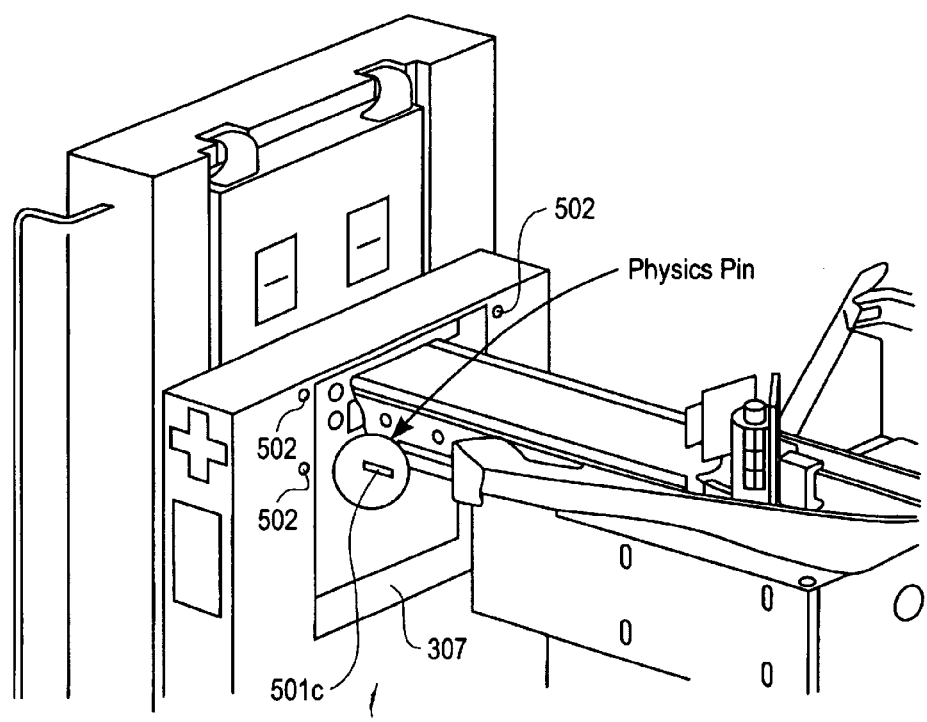
FIG. 5 is a diagram illustrating adjustment of a portal imaging device positioner according to an embodiment of the present invention.

The physics cover 303 is then removed by removing the screws 305A. As will be explained in greater detail below, this allows access to the mounting cavity 307. More particularly, as shown in FIG. 5, a "physics pin" 501c may be installed, to secure the platform 252 to the telescoping boom 256. In addition, bolts 502A that secure the vertical positioner to the telescoping arm are removed. In on embodiment of the invention, four such bolts are provided, only three of which are visible in the figure.

Figure 6:
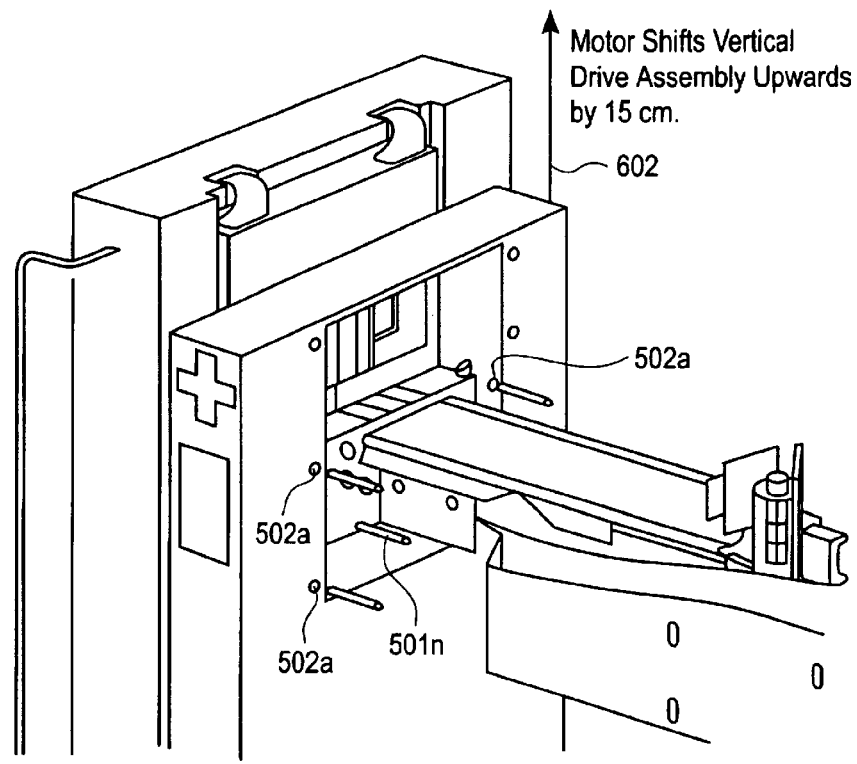
FIG. 6 is a diagram illustrating adjustment of a portal imaging device positioner according to an embodiment of the present invention.
Figure 7:
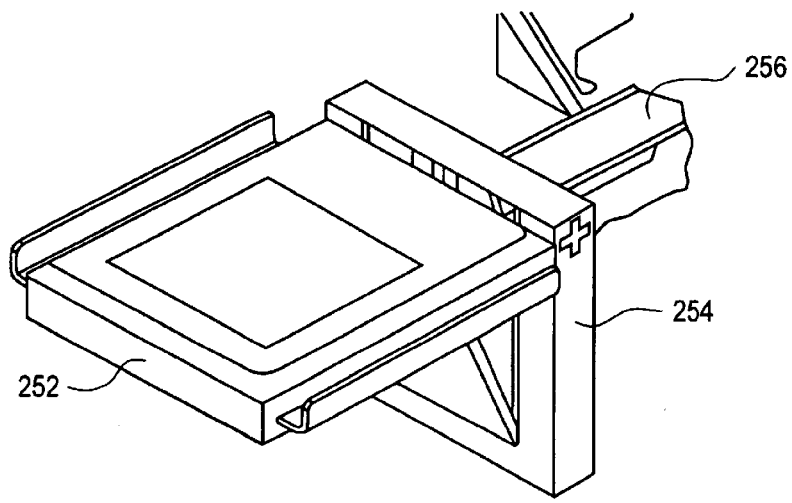
FIG. 7 is a diagram illustrating adjustment of a portal imaging device positioner according to an embodiment of the present invention.

As shown in FIG. 6, removal of the bolts 502A allows the vertical drive assembly to move in the direction of the arrow 602. The presence of the physics pin 501A means that the platform 252 is affixed to the telescoping arm. Thus, the vertical drive assembly 254 moves relative to both. Next, the bolts 502A are replaced and the physics pin 501A is removed. This fixes the vertical drive assembly 254 to the telescoping boom 256 in the physics position. Next, as shown in FIG. 7, the platform 252 may be deployed in a standby position by extending the panel along the hinges 304a, 304b.

Figure 8:
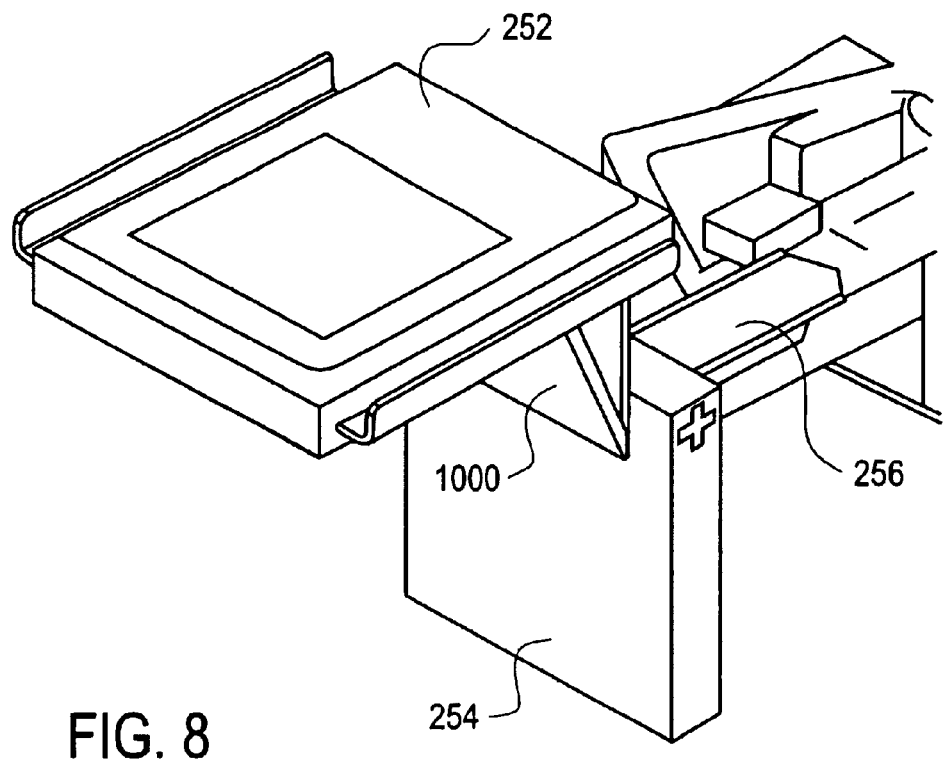
FIG. 8 is a diagram illustrating adjustment of a portal imaging device positioner according to an embodiment of the present invention.
Figure 9:
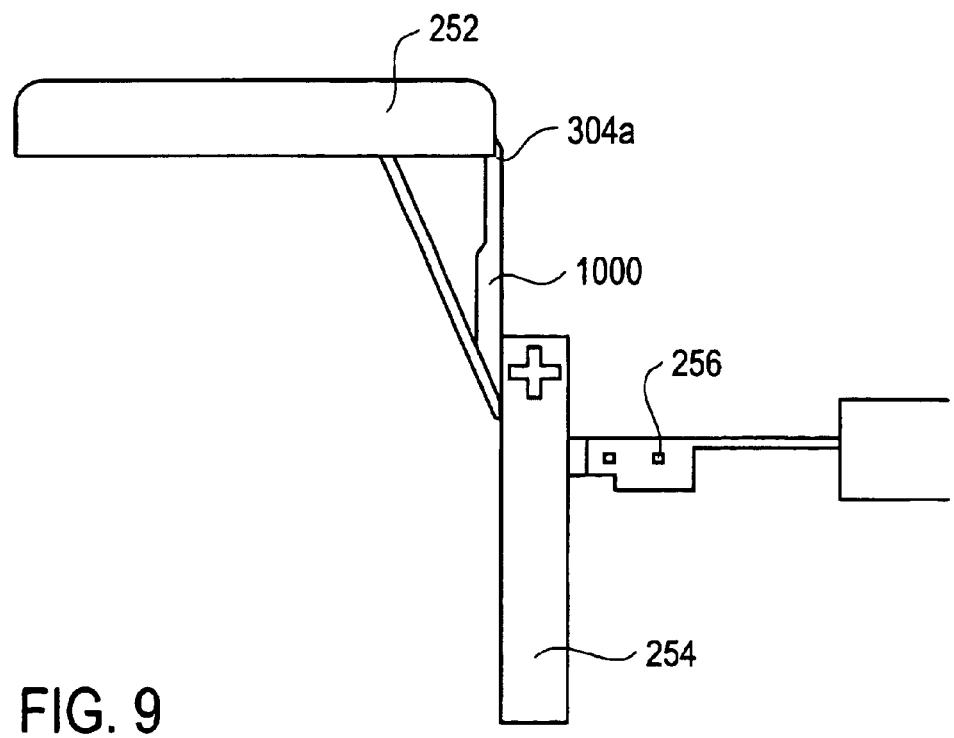
FIG. 9 is a diagram illustrating adjustment of a portal imaging device positioner according to an embodiment of the present invention.

Finally, the panel is deployed in the physics position, as shown in FIGS. 8 and 9. As shown, the portal imaging system includes the deployed horizontal platform 252, extended on the hinges 304a, b.

It is noted that a variety of mechanisms could be employed to position the imaging panel at the patient plane and in the dosimetry position. These include, for example, direct lift systems that do not employ the mounting cavity system described above. Thus, for example, in certain embodiments, the lifting of the platform 252 itself is sufficient to position the panel from the patient dosimetry position to the patient plane. Furthermore, in other embodiments, the platform 252 may be stored horizontally.

Thus, the invention described in the above detailed description is not intended to be limited to the specific form set forth herein, but is intended to cover such alternatives, modifications and equivalents as can reasonably be included within the spirit and scope of the appended claims.

What is claimed is:

1. A portal imaging device positioning apparatus attachable to a radiation therapy device gantry, comprising:
   a support moveably attached to said gantry; and
   a vertically-adjustable portal imaging device positioner adjustably attached to said support, said portal imaging device positioner operable in a first mode and a second mode, wherein in said first mode said portal imaging device positioner maintains an imaging panel in position to receive radiation passing through a body maintained in a patient plane for measuring patient dosimetry during treatment, and wherein in said second mode portal imaging device positioner maintains said imaging panel to receive radiation substantially at said patient plane in a characterization mode for device commissioning for treatment.

2. A portal imaging device positioning apparatus attachable to a radiation therapy device gantry, comprising:
   a support moveably attached to said gantry; and
   a vertically-adjustable portal imaging device positioner adjustably attached to said support, said portal imaging device positioner operable in a first mode and a second mode, wherein in said first mode said portal imaging device positioner maintains an imaging panel in position to receive radiation passing through a body maintained in a patient plane for measuring patient dosimetry during treatment, and wherein in said second mode portal imaging device positioner maintains said imaging panel to receive radiation substantially at said patient plane in a characterization mode for device commissioning for treatment;
   said vertically-adjustable portal imaging device positioner including:
      a vertical drive unit adjustably attached at a mounting cavity to said support; and
      a mounting unit adjustably attached to said vertical drive unit, and adapted to deploy said imaging panel from a vertical position to a horizontal position.

3. A portal imaging device positioning apparatus attachable to a radiation therapy device gantry, comprising:
   a support moveably attached to said gantry; and
   a vertically-adjustable portal imaging device positioner adjustably attached to said support, said portal imaging device positioner operable in a first mode and a second mode, wherein in said first mode said portal imaging device positioner maintains an imaging panel in position to receive radiation passing through a body maintained in a patient plane, and wherein in said second mode portal imaging device positioner maintains said imaging panel to receive radiation substantially at said patient plane;

said vertically-adjustable portal imaging device positioner including:
- a vertical drive unit adjustably attached at a mounting cavity to said support; and
- a mounting unit adjustably attached to said vertical drive unit, and adapted to deploy said imaging panel from a vertical position to a horizontal position;

wherein said vertical drive unit is adjustable in said first mode such that a top of said support is substantially adjacent a top of said mounting cavity, and adjustable in said second mode such that a bottom of said support is substantially adjacent a bottom of said mounting cavity.

4. A portal imaging device positioning apparatus according to claim 3, wherein said imaging panel is adapted to be temporarily secured to said support during an adjustment from said first mode to said second mode.

5. A portal imaging device positioning method, comprising:

adjusting an imaging panel operably secured to a radiation therapy device gantry from a first position in a first mode below a patient plane to a second position in a second characterization mode at a patient plane;

said adjusting comprising:
- temporarily securing a vertically positioned imaging panel to a telescoping support;
- temporarily unsecuring a main drive assembly from said support;
- adjusting said main drive assembly to said second position;
- re-securing said main drive assembly; and
- unsecuring said vertically positioned imaging panel.

6. A portal imaging device positioning method, comprising:

adjusting an imaging panel operably secured to a radiation therapy device gantry from a first position in a first mode below a patient plane to a second position in a second mode at a patient plane, said adjusting comprising:

temporarily securing a vertically positioned imaging panel to a support;

temporarily unsecuring a main drive assembly from said support;

adjusting said main drive assembly to said second position;

re-securing said main drive assembly; and unsecuring said vertically positioned imaging panel said adjusting further comprising:
- adjusting said vertical drive unit in said first mode such that a top of said support is substantially adjacent a top of a mounting cavity on said vertical drive unit; and
- adjusting said vertical drive unit in said second mode such that a bottom of said support is substantially adjacent a bottom of said mounting cavity.

7. A method according to claim 6, further comprising horizontally deploying said imaging panel after said imaging panel has been adjusted to said second position.

8. A portal imaging system, comprising:

a radiation delivery apparatus; and means for deploying an imaging panel in a first mode to receive radiation from said apparatus below a patient plane for device commissioning for treatment and in a second characterization mode at said patient plane for device commissioning for treatment; said deploying means comprising a vertical drive unit adjustably attachable at a mounting cavity to a telescoping support; and a mounting unit adjustably attachable to said vertical drive unit, and adapted to deploy said imaging panel from a vertical position to a horizontal position.

9. A portal imaging system, comprising:

a radiation delivery apparatus; and means for deploying an imaging panel in a first mode to receive radiation from said apparatus below a patient plane and in a second mode at said patient plane, said deploying means comprising:

a vertical drive unit adjustably attached at a mounting cavity to a support; and a mounting unit adjustably attached to said vertical drive unit, and adapted to deploy said imaging panel from a vertical position to a horizontal position;

wherein said deploying means further comprises means for adjusting said vertical drive unit in said first mode such that a top of said support is substantially adjacent a top of said mounting cavity, and in said second mode such that a bottom of said support is substantially adjacent a bottom of said mounting cavity.

10. A system according to claim 9, comprising:

means for temporarily securing said imaging panel to said support; and means for temporarily unsecuring a main drive assembly from said support.

11. A portal imaging device method, comprising:

providing a telescoping support; and providing a vertically-adjustable portal imaging device positioner, said portal imaging device positioner operable in a first mode and a second mode, wherein in said first mode said portal imaging device positioner maintains an imaging panel in position to receive radiation through a body maintained in a patient plane, and wherein in said second mode portal imaging device positioner maintains said imaging panel to receive radiation at said patient plane in a characterization mode.

12. A portal imaging device method, comprising:

providing a telescoping support; and providing a vertically-adjustable portal imaging device positioner, said portal imaging device positioner operable in a first mode and a second mode, wherein in said first mode said portal imaging device positioner maintains an imaging panel in position to receive radiation through a body maintained in a patient plane, and wherein in said second mode portal imaging device positioner maintains said imaging panel to receive radiation at said patient plane in a characterization mode;

said vertically-adjustable portal imaging device positioner including:

a vertical drive unit adjustably attachable at a mounting cavity to said support; and a mounting unit adjustably attachable to said vertical drive unit, and adapted to deploy said imaging panel from a vertical position to a horizontal position.

13. A portal imaging device method, comprising:

providing a support; and providing a vertically-adjustable portal imaging device positioner, said portal imaging device positioner operable in a first mode and a second mode, wherein in said first mode said portal imaging device positioner maintains an imaging panel in position to receive radiation through a body maintained in a patient plane, and wherein in said second mode portal imaging device positioner maintains said imaging panel to receive radiation at said patient plane said vertically-adjustable portal imaging device positioner including:
   a vertical drive unit adjustably attachable at a mounting cavity to said support; and
   a mounting unit adjustably attachable to said vertical drive unit, and adapted to deploy said imaging panel from a vertical position to a horizontal position;

wherein said vertical drive unit is adjustable in said first mode such that a top of said support is substantially adjacent a top of said mounting cavity, and adjustable in said second mode such that a bottom of said support is substantially adjacent a bottom of said mounting cavity.

14. A method according to claim 13, wherein said imaging panel is adapted to be temporarily secured to said support during an adjustment from said first mode to said second mode.

* * * * *